(12) United States Patent
Cheng

(10) Patent No.: US 7,278,427 B2
(45) Date of Patent: Oct. 9, 2007

(54) FILTERED BREATHING DEVICE WITH AROMATIC-INFUSION

(76) Inventor: Hin Yee Cheng, Flat E, 18/F., Man Kwong Court, 12F Smithfield Road, Kennedy Town, Sai Wan (HK)

( * ) Notice: Subject to any disclaimer, the term of this patent is extended or adjusted under 35 U.S.C. 154(b) by 500 days.

(21) Appl. No.: 10/899,952

(22) Filed: Jul. 26, 2004

(65) Prior Publication Data

US 2005/0022805 A1    Feb. 3, 2005

(30) Foreign Application Priority Data

Sep. 26, 2003  (HK)  ................................. 03106940
Apr. 15, 2004  (CN)  ...................... 2004 2 00510538

(51) Int. Cl.
*A61M 15/00*  (2006.01)
*A61M 16/10*  (2006.01)

(52) U.S. Cl. .............................. 128/203.16; 128/203.12
(58) Field of Classification Search ........... 128/206.11, 128/206.12, 206.15, 206.17–206.19, 206.21, 128/205.27, 205.29, 203.12, 203.23, 207.18
See application file for complete search history.

(56) References Cited

U.S. PATENT DOCUMENTS

| 3,949,743 A | * | 4/1976 | Shanbrom | 128/200.14 |
| 3,964,478 A | * | 6/1976 | Kropfhammer | 128/203.12 |
| 5,313,821 A | * | 5/1994 | Bett et al. | 73/23.34 |
| 6,513,524 B1 | * | 2/2003 | Storz | 128/203.26 |
| 7,108,659 B2 | * | 9/2006 | Ross et al. | 600/529 |
| 2005/0016553 A1 | * | 1/2005 | Iannuzzi | 131/273 |

* cited by examiner

Primary Examiner—Justine R. Yu
Assistant Examiner—Kristen Matter
(74) Attorney, Agent, or Firm—Alix, Yale & Ristas, LLP

(57) ABSTRACT

A breathing device includes a housing having an air inlet port, a filtered air outlet port, and a filter situated upstream of the outlet port and downstream of the inlet port. An inhalation valve is situated upstream of the outlet port and downstream of the filter and allows inhalation airflow toward the outlet port, but not vice versa. An aroma-effuser is situated upstream of the inhalation valve and downstream of the filter and entrains aroma in the airflow to be inhaled.

11 Claims, 6 Drawing Sheets

US 7,278,427 B2

FILTERED BREATHING DEVICE WITH AROMATIC-INFUSION

BACKGROUND OF THE INVENTION

The present invention relates to a device through which one can inhale filtered aromatic air. More particularly, although not exclusively, the invention relates to a breathing/filtering device to be held in front of a user's face and comprising a face piece through which the user can both inhale aroma-infused air, and exhale without displacement of the face piece from the face.

It is known to wear filtration masks in hospitals for example. Some masks simply provide one or more layers of material strapped across the mouth and nose. Some include a one-way valve through which exhaled air passes freely to atmosphere.

The filtration elements often have an unpleasant "chemical odour" and prolonged use of masks having such filters can be uncomfortable and headache-inducing. Furthermore, a patient in a hospital might benefit from inhaling herbal aroma during use of a filtration device.

OBJECTS OF THE INVENTION

It is an object of the present invention to overcome or substantially ameliorate at least one of the above disadvantages and/or more generally to provide a filtered breathing device with built-in aromatic infusion to filtered air to be inhaled through a face piece.

DISCLOSURE OF THE INVENTION

There is disclosed herein a breathing device comprising:
a housing having an air inlet port,
a filtered air outlet port,
a filter situated upstream of the outlet port and downstream of the inlet port,
an inhalation valve situated upstream of the outlet port and downstream of the filter and adapted to allow inhalation airflow toward the outlet port, and
an aroma-effuser situated upstream of the inhalation valve and downstream of the filter and adapted to entrain aroma in said airflow.

Preferably, the breathing device further comprises an exhalation exhaust valve situated upstream of the outlet port and downstream of the inhalation valve and adapted to release exhaled air to atmosphere.

Preferably, the breathing device further comprises a main body and a resilient face piece attached to the main body and upon which the outlet port and exhaust port are situated.

Preferably, the face piece has a curved front profile adapted to fits snugly under a user's nose.

Preferably, the breathing device further comprises a pair of said exhaust ports and corresponding exhaust valves at opposed lateral positions upon the face piece.

Preferably, the breathing device further comprises a resilient exhaust valve formed integrally with the face piece and covering the exhaust port.

Preferably, the inhalation valve comprises a resilient flap secured to a plate through which said airflow passes.

Preferably, the breathing device further comprises an exhaust seat extending from the plate and having an exhaust passage therethrough, which passage in covered by the exhaust valve.

Preferably, the breathing device further comprises a main body housing the filter, and wherein the aroma effuser comprises a chamber formed in the main body and adapted to receive aromatic herbs, the chamber having a perforated wall in communication with said airflow.

Preferably, the chamber comprises a removable cover accessible from the main body exterior.

Preferably, the filter comprises one or more filtration elements selected from the group consisting of a fabric sheet, activated carbon and corrugated paper.

BRIEF DESCRIPTION OF THE DRAWINGS

Preferred forms of the present invention will now be described by way of example with reference to the accompanying drawings, wherein.

DESCRIPTION OF THE PREFERRED EMBODIMENT

Figure 1:
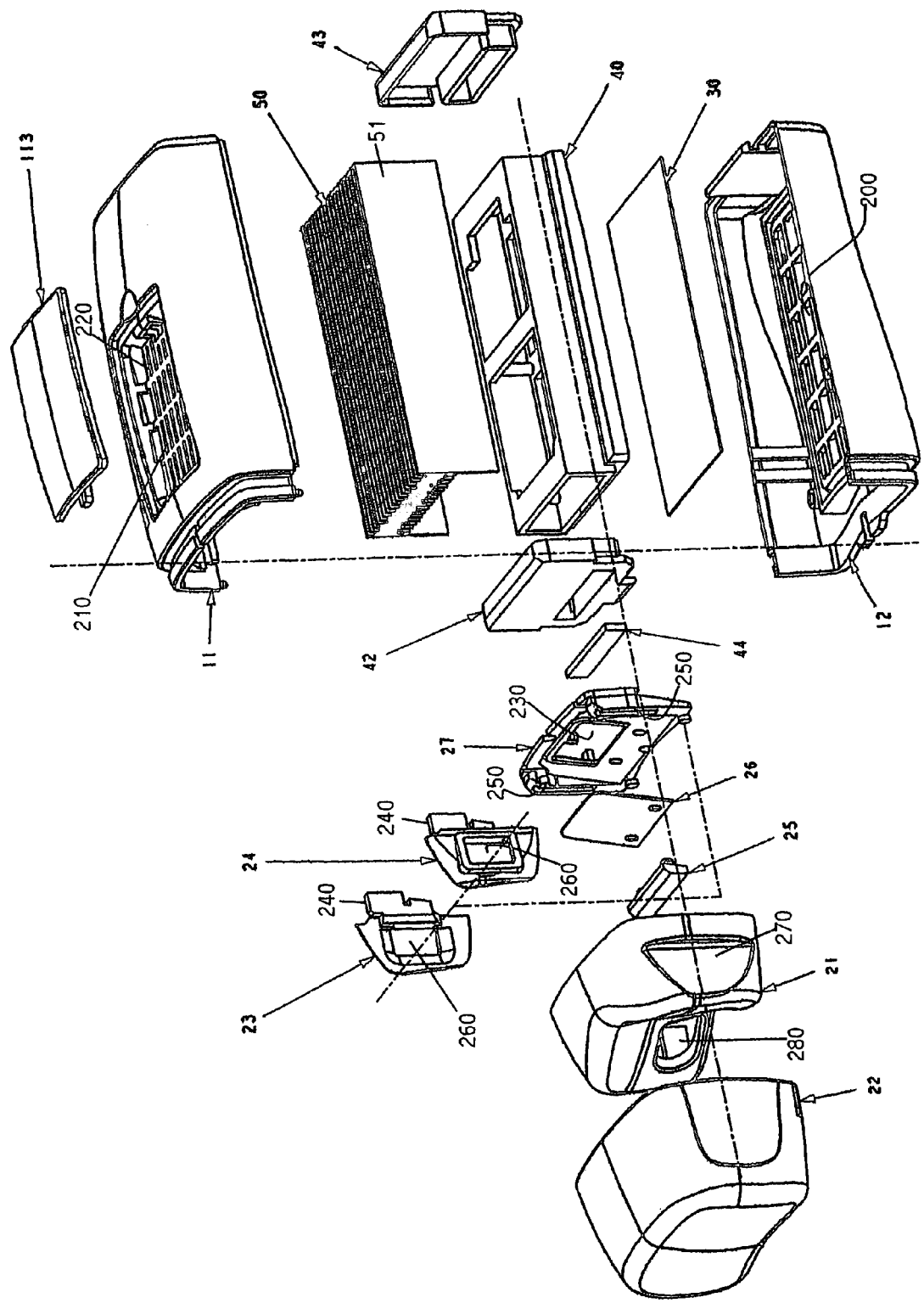
FIG. 1 is a schematic parts-exploded perspective illustration of a breathing device.
Figure 2:
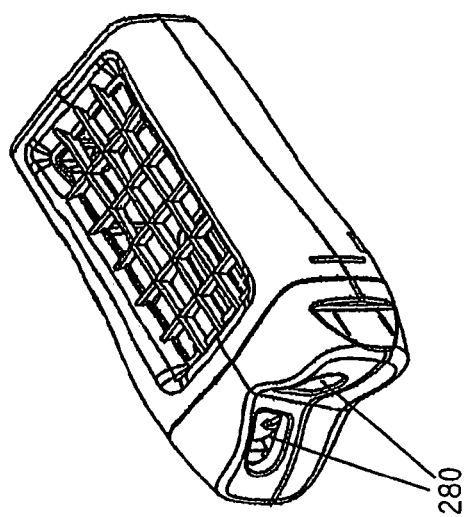
FIG. 2 is a schematic inverted perspective illustration of the assembled breathing device, FIG. 3 in a schematic perspective illustration of the assembled breathing device, FIG. 4 in a schematic plan view of the breathing device.
Figure 3:
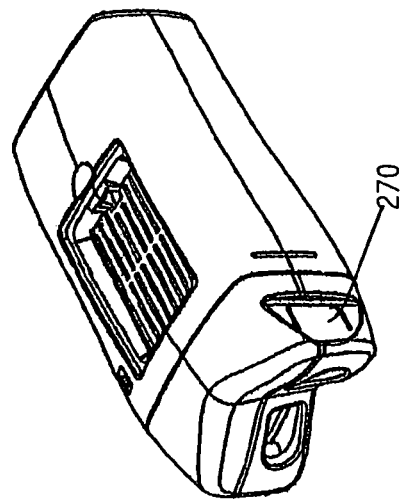
Figure 6:
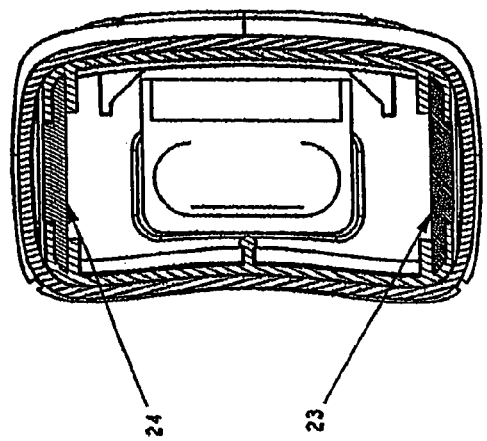
FIG. 6 is a schematic cross-sectional elevation of the breathing device taken at VI-VI in FIG. 4.
Figure 7:
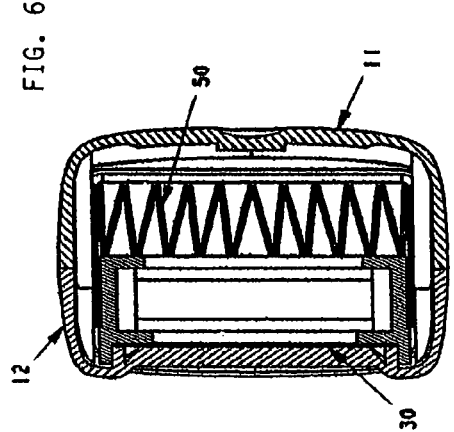
FIG. 7 is a schematic cross-sectional elevation of the breathing device taken at VII-VII in FIG. 4.
Figure 5:
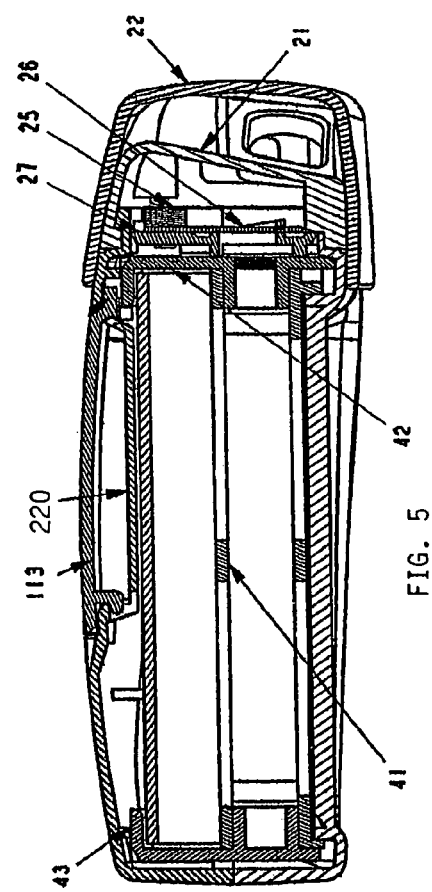
FIG. 5 is a schematic cross-sectional elevation of the breathing device taken at V-V in FIG. 4.
Figure 4:
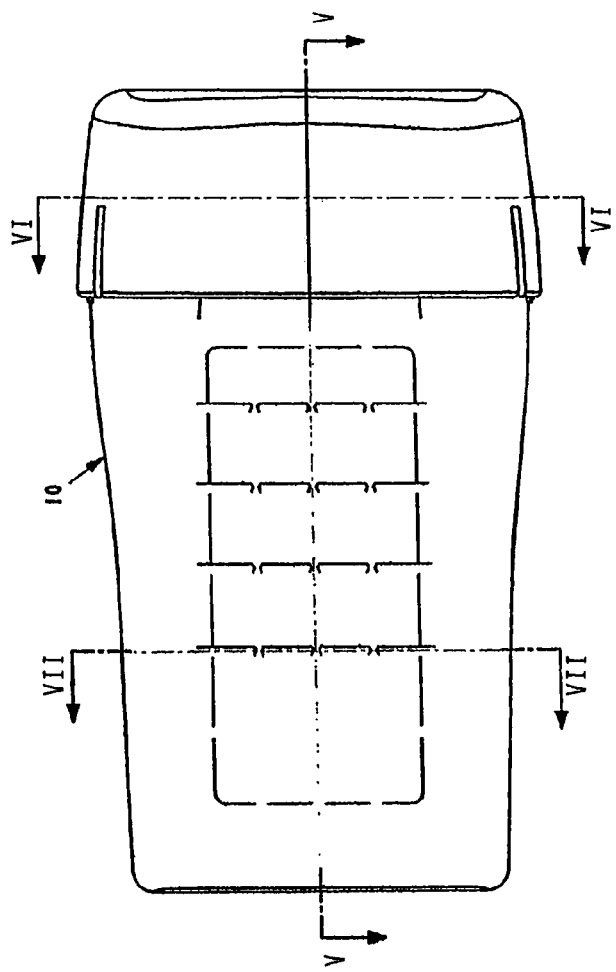
Figure 8:
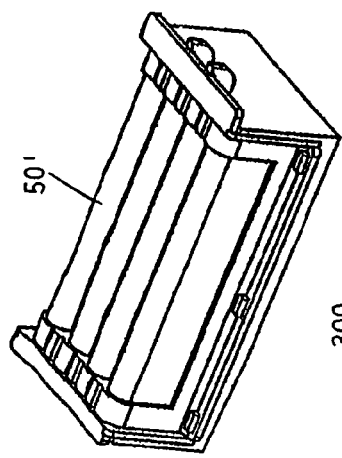
FIG. 8 is a schematic perspective illustration of an alternative filter module.
Figure 10:
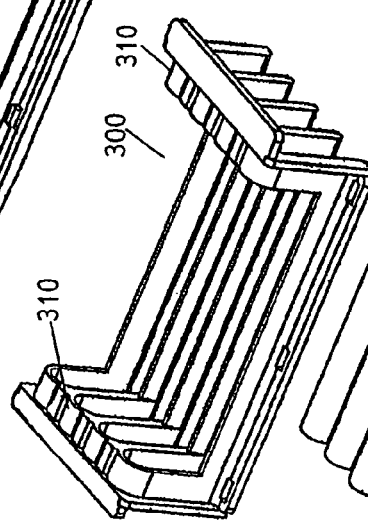
FIG. 10 is a schematic perspective illustration of a filter paper-support frame, forming part of the module of FIG. 8.
Figure 11:
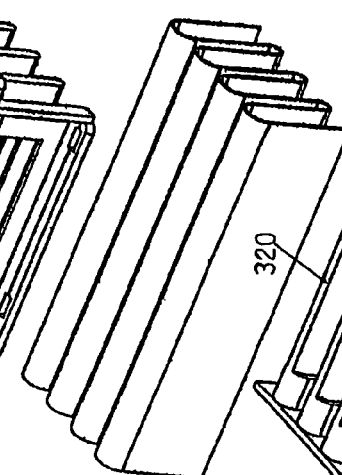
FIG. 11 is a schematic perspective illustration of a corrugated filter paper forming part of the module of FIG. 8.

FIGS. 1 to 7 of the accompanying drawings depict schematically various components forming a breathing device. Device is typically small enough to fit within one's pocket. These components include a main body upper 11 and a main body lower 12 each formed of moulded plastics material and adapted to fit together to form a main body that houses various filtration elements to be described. Fitted to the front end of the main body is a resilient plastics face piece 21 that can be held against the lips of a user. A cap 22 can fit over the face piece 21 when the device is not in use.

The main body lower 12 has a grid opening defining an air inlet port 200. Positioned above the grid is a gauze filter 30 typically formed of nonwoven fabric material.

Positioned above the gauze 30 in an activated carbon (or other chemical) filter box 40 that would contain activated carbon (not shown).

Positioned above the activated carbon filter box 40 is a corrugated paper filter element 50 having side portions 51 that depend therefrom and extend down the opposed lateral sides of the activated carbon filter box 40. End plates 42 and 43 are fitted to the ends of the three filter elements 30, 40 and 50 to form an overall "triple filter" replaceable cartridge.

The main body upper 11 includes a chamber 210 having a perforated bottom wall 220. The perforated bottom wall is exposed to the upper surface of the corrugated paper filter 50. A cover 113 fits over the chamber 210.

Situated between the filter module and the face piece 21 is a valve plate 27 fixed in place between the main body upper 11 and main body lower 12. The valve plate 27 has an opening 230 through which air from above the corrugated paper filter 50 and below the chamber bottom wall 220 is drawn toward the face piece 21. Fitted over the opening 230 in a resilient inhalation valve 26 in the form of a flap held in place by a retainer 25. The flap would typically be formed of soft rubber sheet or soft plastics sheeting. The retainer 25 comprises a pair of lugs passing through a corresponding pair of apertures in the inhalation valve 26 and received tightly within a pair of corresponding holes in the valve plate 27 as shown.

Flanking the inhalation valve 26 at either side is a pair of exhaust seats 23 and 24. These comprise tabs 240 that fit within slots 250 on the front face of the valve plate 27. Both the valve plates 27 and exhaust seats 23 and 24 are formed of rigid plastics material. Each exhaust seat 23, 24 comprises an exhaust port 260 passing therethrough. The soft plastics face piece 21 incorporates a pair of laterally opposed exhaust valves in the form of resilient flaps 270 formed integrally therewith. Each flap 270 is integrally hinged at its back edge to a sidewall of the face piece 21. These flaps naturally close upon the exhaust ports 260.

The face piece comprises a pair of filtered air outlets 280 through which filtered air passes upon the inhalation of a user having the face piece 21 positioned under the bottom of his or her nose—enabling the user to speak clearly while using the device.

Figure 13:
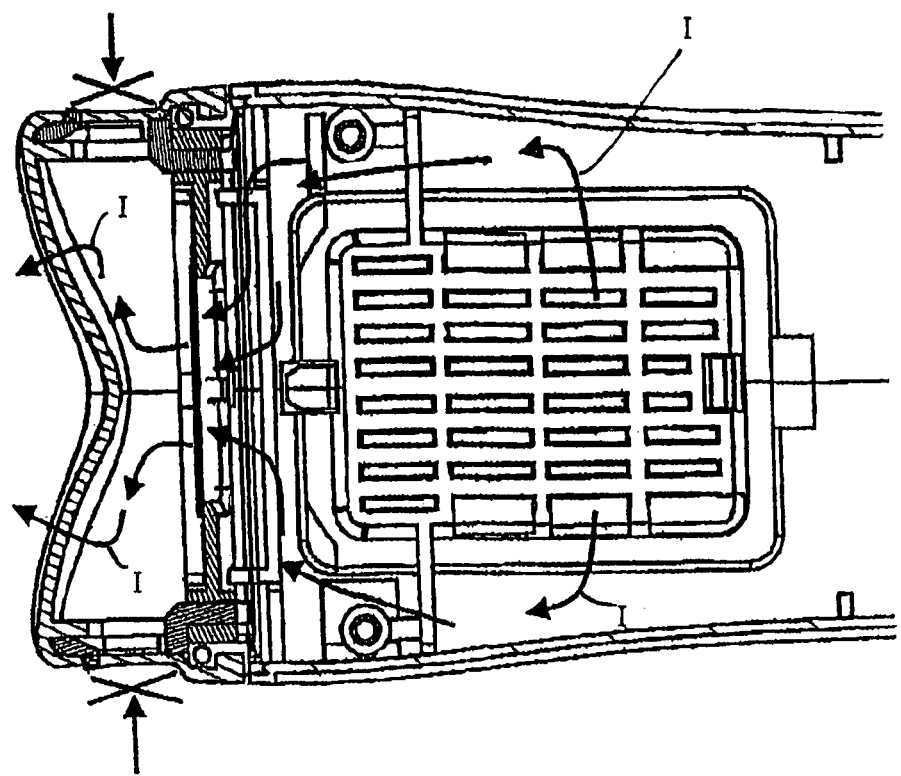
FIG. 13 is a schematic cross-sectional elevational view of part of the breathing device of FIGS. 1 to 7 showing the inhalation airflow path therethrough.
Figure 14:
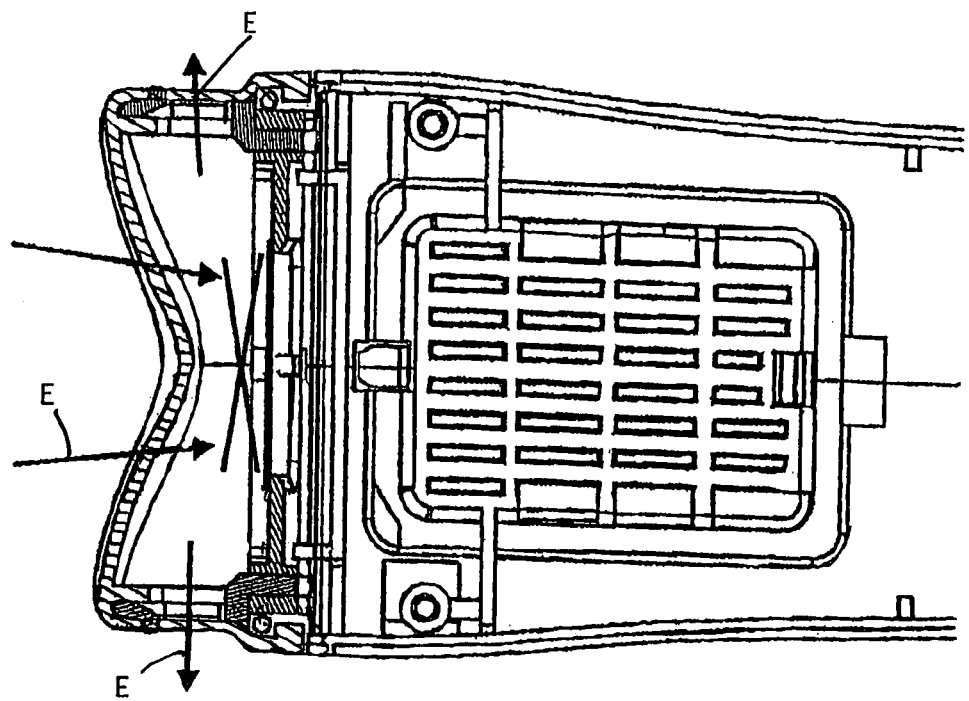
FIG. 14 is a schematic cross-sectional elevational view of part of the breathing device of FIGS. 1 to 7 showing the exhalation airflow path therethrough.
Figure 15:
FIG. 15 is a schematic illustration of a person using the breathing device.

Upon inhalation, the inhalation valve 26 opens as air is drawn through from above the corrugated paper filter 50. There might be aromatic herbs placed within the herb chamber 210 and the aroma exuding therefrom will migrate through the perforated floor 220 into the airflow drawn from above the corrugated filter paper 50 and past the inhalation valve 26 to the face piece. During inhalation, the exhaust valve flaps 270 will remain closed upon the exhaust seats 23 and 24. The airflow path is indicated by arrows I in FIG. 13. Upon exhalation, the inhalation valve 26 is closed upon the valve plate 27 and the exhaust flaps 270 will open to enable exhaled air to escape to atmosphere from the face piece 21, without flowing back into the filtration unit. The exhalation airflow path is indicated by arrows E in FIG. 14.

Figure 12:
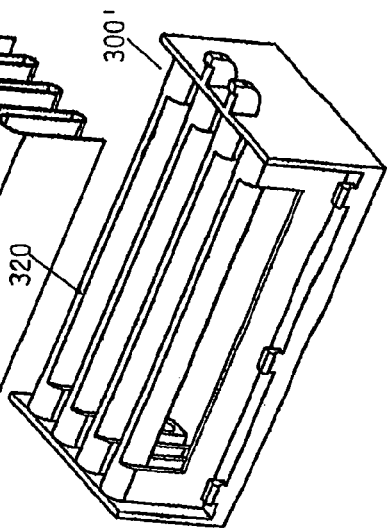
FIG. 12 is a schematic perspective illustration of a further alternative filter paper-support frame.
Figure 9:
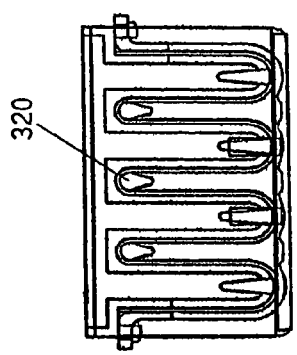
FIG. 9 is a schematic cross-sectional and elevation of the filter module of FIG. 8.

FIGS. 8 to 11 show an alternative construction of filter module which instead of comprising a pair of separate end plates 42 and 43, has these components formed integrally with a paper filter element support frame 300. In this embodiment, the corrugated filter paper 50' takes on a curved profile form and fits over a pair of profiled end formers 310. In the embodiment of FIG. 12, the formers extend throughout the full-length of the support frame 300' with a number of ribs 320 as shown to support the corrugated filter paper.

The devices disclosed herein have many applications including use for poison chemical attacks, in places of heavy smoke or outdoor places having heavy traffic pollution, or places where other people are smoking. It could also simply be used for aromatherapy or for the breathing exercises.

It should be appreciated that modifications and alterations obvious to those skilled in the art are not to be considered as beyond the scope of the present invention. For example, instead of stacking three different filter types one above the other, these could be positioned lengthwise along the main body.

The invention claimed is:

1. A breathing device comprising:
   a housing having an air inlet port,
   a filtered air outlet port,
   a filter situated upstream of the outlet port and downstream of the inlet port,
   an inhalation valve situated upstream of the outlet port and downstream of the filter and adapted to allow inhalation airflow toward the outlet port, and
   an aroma-effuser situated upstream of the inhalation valve and downstream of the filter and adapted to entrain aroma in said airflow.

2. The breathing device of claim 1, further comprising an exhaust port with an exhalation exhaust valve situated upstream of the outlet port and downstream of the inhalation valve and adapted to release exhaled air to atmosphere.

3. The breathing device of claim 2, further comprising a main body and a resilient face piece attached to the main body and upon which the outlet port and exhaust port are situated.

4. The breathing device of claim 3, wherein the face piece has a curved front profile adapted to fits snugly under a user's nose.

5. The breathing device of claim 3, further comprising a resilient exhaust valve formed integrally with the face piece and covering the exhaust port.

6. The breathing device of claim 5, comprising a pair of said exhaust ports and corresponding exhaust valves at opposed lateral positions upon the face piece.

7. The breathing device of claim 5, wherein the inhalation valve comprises a resilient flap secured to a plate through which said airflow passes.

8. The breathing device of claim 6, further comprising an air exhaust seat extending from a plate and having an exhaust passage therethrough, which passage is covered by one of the pair of exhaust valves.

9. The breathing device of claim 1, further comprising a main body housing the filter, and wherein the aroma effuser comprises a chamber formed in the main body and adapted to receive aromatic herbs, the chamber having a perforated wall in communication with said airflow.

10. The breathing device of claim 9, wherein the chamber comprises a removable cover accessible from the main body exterior.

11. The breathing device of claim 1, wherein the filter comprises one or more filtration elements selected from the group consisting of a gauze sheet, activated carbon and corrugated paper.

* * * * *